United States Patent
Lykins

(10) Patent No.: US 12,357,482 B2
(45) Date of Patent: Jul. 15, 2025

(54) URETERAL STENT REMOVAL DEVICES, SYSTEMS, AND METHODS

(71) Applicant: L and L Medical, LLC, Gainesville, GA (US)

(72) Inventor: Lawrence E. Lykins, Gainesville, GA (US)

( * ) Notice: Subject to any disclaimer, the term of this patent is extended or adjusted under 35 U.S.C. 154(b) by 0 days.

(21) Appl. No.: 18/479,704

(22) Filed: Oct. 2, 2023

(65) Prior Publication Data

US 2024/0156625 A1     May 16, 2024

Related U.S. Application Data

(60) Provisional application No. 63/475,501, filed on Nov. 15, 2022.

(51) Int. Cl.
*A61F 2/95*     (2013.01)
*A61B 17/22*     (2006.01)
*A61F 2/04*     (2013.01)

(52) U.S. Cl.
CPC .......... *A61F 2/95* (2013.01); *A61B 17/22031* (2013.01); *A61B 2017/22035* (2013.01); *A61F 2002/048* (2013.01); *A61F 2002/9528* (2013.01)

(58) Field of Classification Search
CPC ............... A61F 2/95; A61F 2002/9505; A61F 2002/9511; A61F 2002/048; A61B 2017/00623; A61B 2017/22035; A61B 17/32056; A61B 17/221; A61B 17/3468; A61B 2017/2204
See application file for complete search history.

(56) References Cited

U.S. PATENT DOCUMENTS

| | | | | |
|---|---|---|---|---|
| 5,520,697 | A * | 5/1996 | Lindenberg | A61F 2/95 606/108 |
| 5,713,948 | A * | 2/1998 | Uflacker | A61F 2/966 623/1.23 |
| 2002/0120277 | A1* | 8/2002 | Hauschild | A61F 2/95 606/108 |
| 2007/0198002 | A1* | 8/2007 | Melsheimer | A61B 17/3468 606/1 |
| 2008/0071287 | A1* | 3/2008 | Goto | A61F 2/95 600/153 |
| 2008/0221582 | A1* | 9/2008 | Gia | A61B 17/221 606/108 |
| 2008/0262592 | A1* | 10/2008 | Jordan | A61F 2/95 623/1.11 |
| 2010/0262157 | A1* | 10/2010 | Silver | A61F 2/95 623/1.11 |
| 2017/0136222 | A1* | 5/2017 | Hakim | A61F 2/94 |
| 2018/0085129 | A1* | 3/2018 | Hamuro | A61F 2/01 |

\* cited by examiner

*Primary Examiner* — Sarah W Aleman
(74) *Attorney, Agent, or Firm* — Troutman Pepper Locke LLP; Ryan A. Schneider

(57) ABSTRACT

A passive stent removal device, system and method using a series of capturing steps to grasp a stent smoothly and consistently for removal.

9 Claims, 8 Drawing Sheets

URETERAL STENT REMOVAL DEVICES, SYSTEMS, AND METHODS

CROSS-REFERENCE TO RELATED APPLICATIONS

This application claims the benefit under 35 USC § 119(e), of U.S. Provisional Patent Application No. 63/475,501, filed 15 Nov. 2022, the entire contents and substance of each being incorporated herein by reference in its entirety as if fully set forth below.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

SEQUENCE LISTING

Not Applicable

STATEMENT REGARDING PRIOR DISCLOSURES BY THE INVENTOR OR A JOINT INVENTOR

Not Applicable

BACKGROUND OF THE DISCLOSURE

1. Field of the Disclosure

The present disclosure relates generally to the field urology, and more particularly, the present disclosure relates to a grasper used for removal of ureteral stents from the urinary system.

2. Background

Ureteral stents are used to create a pathway for urinary drainage from the kidney to the bladder in patients with ureteral obstruction or injury or to protect the integrity of the ureter in a variety of surgical manipulations. A number of clinical conditions can produce interruption in urine flow including, for example, intrinsic obstruction of the ureter due to tumor growth, stricture or stones, compression of the ureter due to extrinsic tumor growth, stone fragment impactation in the ureter following extracorporeal shock wave lithotripsy (ESWL), and ureteral procedures such as ureteroscopy and endopyelotomy.

A ureteral stent is a device designed to restore the flow of urine by creating a pathway for urinary drainage from the kidney to the bladder. To treat obstructions of urine flow, stents can avoid obstructions of the ureter (e.g., ureteral stones, ureteral tumors, etc.) that disrupt the flow of urine from the corresponding kidney to the bladder. In other surgical applications, ureteral stents can be used to enhance or protect the integrity of the ureter.

Ureteral stents typically are tubular in shape, terminating in two opposing ends: a kidney proximal end and a urinary bladder distal end. One or both of the ends of the stent may be coiled in a pigtail spiral or J-shape to prevent the upward and/or downward migration of the stent in the lumen of the ureter due, to day-to-day physical activity of the patient, for example. A kidney end coil is designed to retain the stent within the renal pelvis and to prevent stent migration down the ureter. The urinary bladder end coil is positioned in the bladder and is designed to prevent stent migration upward toward the kidney. The bladder end-coil is also used to aid in retrieval and removal of the stent.

A ureteral stent is not permanent and needs to be replaced periodically. The length of time a stent is left in place is referred to as an indwelling time, and is generally determined by the indication for placement and by physician experience. Indwelling times can range from a few days for relief of ureteral edema to the duration of the patient's life for maintenance of ureteral patency in case of obstruction from malignant disease. Manufacturers usually recommend exchange of stents at three to six month intervals, and studies have shown that the prevalence of complications increases with longer indwelling times.

Placement of the stent and leaving the stent in place for too long can lead a multitude of discomforts and complications. Consequences of ureteral stent placement can include irritative bladder symptoms, which can be intolerable and require early stent removal. Some complications of ureteral stents include, but are not limited to, urinary tract infections, malposition, migration, encrustation, and ureteral erosion or fistulation.

Malposition is defined as an incorrect position of a stent relative to initial placement. Stents made of stiffer materials may penetrate the ureter, collecting system, and kidney parenchyma during placement, resulting in urinoma (a mass formed by encapsulated extravasated urine) or hematoma formation. Migration of the stent within the urinary tract may also occur.

There are two common ways to remove a ureteral stent. Prior to removal, if the stent has been in place for a while, an X-ray is used to see if the stent is smooth or if it has become lined with a crust because the crust can make it harder to remove the stent. First, some stents can be removed with an attached string that comes out of the urethra. In some cases, a patient will be able to remove the stent via the string at home, while in other cases, a doctor will remove the stent at their office or a hospital.

Second, if the ureteral stent has no string, a removal procedure is required to remove the stent. The general procedure is conducted using a thin, lighted tube called a cystoscope, which may require general anesthesia. Ureteroscopes can be used as well. The doctor inserts the cystoscope into the urethra and on into the bladder. The scope allows the doctor to check areas of the bladder and urethra that usually don't show up well on X-rays. Next, the doctor will insert tiny tools through the cystoscope to remove the stent.

Most of these retrieval devices use opposing jaws at a proximal end to grasp via an opening/closing of the jaws about a portion of the stent. A handle at a distal end of the device is used to control jaw actuation.

Commercially available stents simply can be difficult to remove, especially from male patients. The above-noted methods for removal of an indwelling stent from the ureter of a male are complex and painful procedures which can require a general anesthetic.

What is needed, therefore, is a stent grasping technology that overcomes the disadvantages of the conventional art. Embodiments of the present disclosure address this need as well as other needs that will become apparent upon reading the description below in conjunction with the drawings.

BRIEF SUMMARY OF THE DISCLOSURE

In an exemplary embodiment, the present invention is a passive stent removal device, system and method using a series of capturing steps to grasp a stent smoothly and consistently for removal. A proximal end of a grasper device is cooperatively shaped with a loop and ball to, through capture steps, move through various orientations to capture and remove a captured stent without using jaws or other potentially dangerous designs of capture.

In an exemplary embodiment, the present invention is a passive stent removal device comprising a grasper instrument having a body portion between a proximal end configured to engage a stent for removal from a body and a distal end configured to pass through a delivery device, wherein the proximal end is a passive engagement end free of independently moving components while configured to capture at least a portion of the stent via manipulation of the distal end of the grasper instrument through one or more actions selected from the group consisting of a pushing action, a pulling action, a twisting action, and a combination thereof, and remove the stent from the body.

In any embodiment of the present invention, the proximal end of the grasper instrument can comprise a first proximal end portion that shares a common central axis with, and extends in the same direction as, the body portion.

In any embodiment of the present invention, the proximal end of the grasper instrument can further comprise a second proximal end portion with a capture unit, the second proximal end portion extending in at least an approximately opposite direction from the first proximal end portion.

In any embodiment of the present invention, the proximal end of the grasper instrument can further comprise a u-shaped proximal end portion connecting the first proximal end portion to the second proximal end portion.

In any embodiment of the present invention, the passive engagement end free of independently moving components has a loop width defined as the distance between the first proximal end portion and the second proximal end portion.

In any embodiment of the present invention, the passive engagement end free of independently moving components has a capture opening width defined as the smallest distance between the capture unit and the first proximal end portion.

In any embodiment of the present invention, the capture unit can comprise a sphere formed at the second proximal end portion.

In any embodiment of the present invention, the loop width can be between 0.1-0.2 inches.

In any embodiment of the present invention, the capture opening width can be between 0.062-0.072 inches.

In any embodiment of the present invention, the grasper instrument can comprise series stainless steel wire.

In any embodiment of the present invention, the delivery device can be selected from a group consisting of a cystoscope and an ureteroscope.

In any embodiment of the present invention, the passive engagement end free of independently moving components is free of actuated elements capable of movement independent from the manipulation of the distal end of the grasper instrument.

In another exemplary embodiment, the present invention is a passive stent removal device free of independently actuatable elements comprising a grasper instrument comprising a body portion extending along a body axis, a passive grasper end, and a distal manipulation end, wherein the body portion extends a both length between the passive grasper end and the a distal manipulation end, wherein the passive grasper end is configured to engage a stent for removal from a body without independently actuatable elements to capture the stent, and wherein the distal manipulation end is configured to pass through a scope device, wherein the grasper instrument is of unitary construction such that through capture steps, manipulation of the distal manipulation end manipulates the distal manipulation end through orientations enabling the distal manipulation end to engage with at least a portion of a stent, capture at least a portion of the stent so it can be removed from the body, and remove the captured stent with the passive grasper end.

In any embodiment of the present invention, the passive grasper end of the grasper instrument can comprise a first proximal end portion that shares the body axis and extends in the same direction as the body portion, a second proximal end portion terminating at a ball end, the second proximal end portion extending in an opposite direction from the first proximal end portion, and a loop proximal end portion connecting the first proximal end portion to the second proximal end portion, wherein the passive grasper end has a loop width defined as the distance between the first proximal end portion and the second proximal end portion, and wherein the passive grasper end has a capture opening width defined as the smallest distance between an outer surface of the ball end and the first proximal end portion.

In any embodiment of the present invention, the loop width can be between 0.1-0.2 inches and the capture opening width can be between 0.062-0.072 inches.

In any embodiment of the present invention, the scope device can be selected from a group consisting of a cystoscope and an ureteroscope, and the distal manipulation end can be further configured to be operatively connected to a tool holding device through which an operator manipulates of the distal end of the grasper instrument through one or more actions selected from the group consisting of a pushing action, a pulling action, a twisting action, and a combination thereof.

In any embodiment of the present invention, the tool holding device comprises a pin vise.

In another exemplary embodiment, the present invention is a method of stent removal using an exemplary device comprising inserting the proximal end of the grasper instrument into a body passage leading to a stent, back loading the distal end of the grasper instrument through the delivery device, capturing a portion of the stent via manipulation of the distal end such that the captured portion of the stent fits through the capture opening width and into a loop portion of the grasper instrument defined by the first proximal end portion, the second proximal end portion, and the u-shaped proximal end portion, and removing the captured stent from the body passage via a pulling action at the distal end.

In another exemplary embodiment, the present invention is a method of grasping comprising inserting a portion of a grasping device into a urinary system of a body, backing loading a portion of the grasping device though a scope device, placing a pin vise about a distal end of grasping device to control the orientation of a proximal end within the body, capturing a portion of a stent located in the body in a loop portion of the proximal end, and removing the grasping device and the stent from the urinary system.

These and other aspects of the present disclosure are described in the Detailed Description below and the accompanying figures. Other aspects and features of embodiments of the present disclosure will become apparent to those of ordinary skill in the art upon reviewing the following description of specific, exemplary embodiments of the present invention in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The accompanying drawings, which are incorporated in and constitute a part of this specification, illustrate multiple embodiments of the presently disclosed subject matter and explain the principles of the presently disclosed subject matter. The drawings are not intended to limit the scope of the presently disclosed subject matter in any manner.

DETAILED DESCRIPTION

Figure 1:
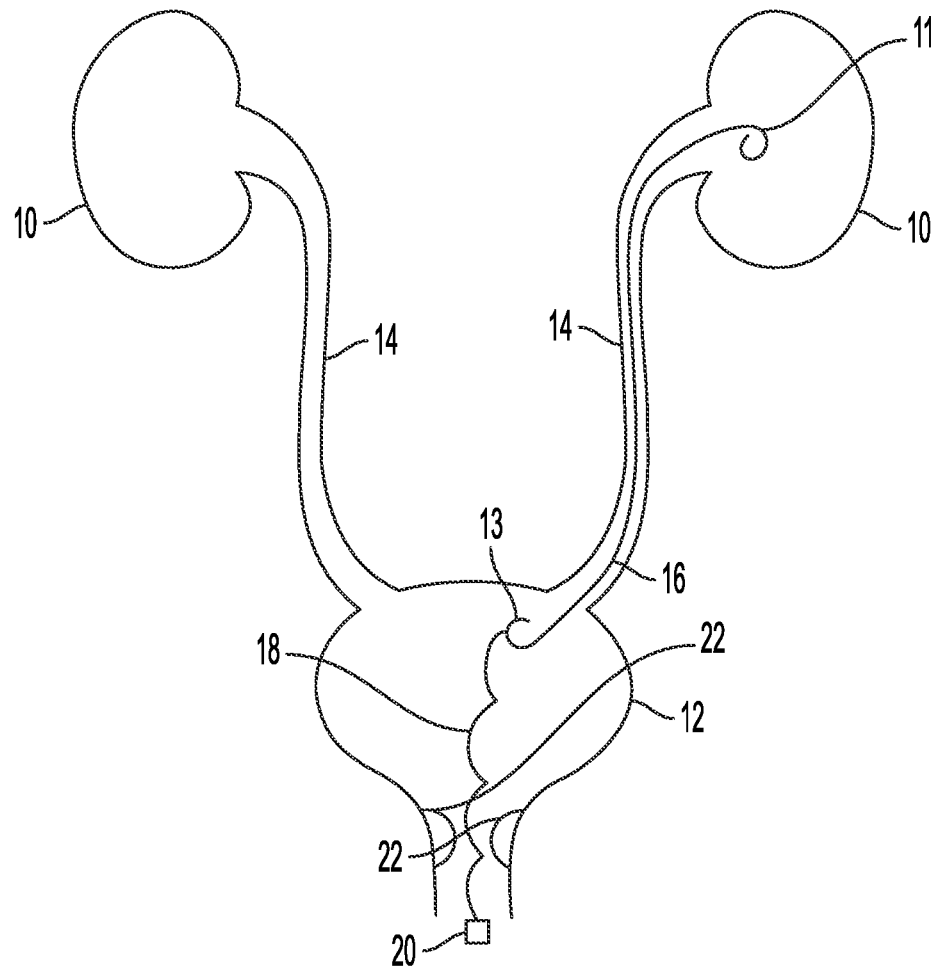
FIG. 1 schematically illustrates an exemplary urinary system with a stent and grasper shown in relative positions.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or conducted in many ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

Referring to FIG. 1, a stent 16 (which may be made of polymers or a number of materials), with opposing curls 11, 13 at its ends, is shown in place in ureter 14. One end and curl 13 of stent 16 lies in bladder 12 and the opposing end and curl 11 lies in kidney 10.

The curls 11 and 13 assist in keeping stent 16 in place in ureter 14. The curls 11 and 13 can be J-shaped or more curled than the curls 11 and 13 shown, and may be curled to define less than one complete circle, about one complete circle, exactly one complete circle, or more than one complete circle from a side view.

Figure 6:
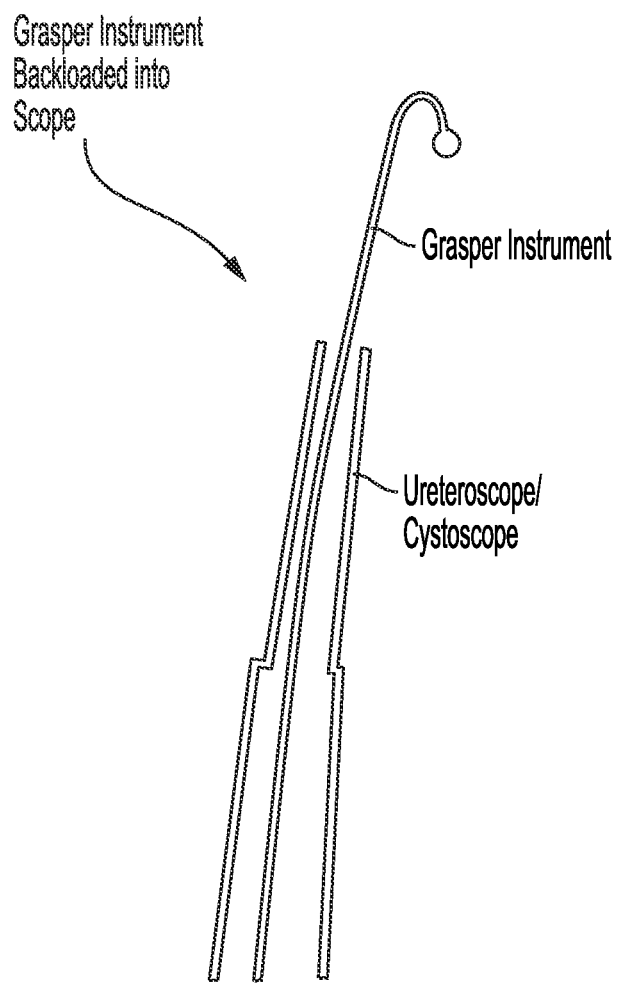
FIG. 6 illustrates backloading the grasper instrument into a scope according to some examples of the present disclosure.

As shown in FIG. 6, the present invention 18 is configured to envelop an end of stent 16 residing in bladder 12, being backloaded though a delivery device 20, for example, a cystoscope or ureteroscope.

Figure 2:
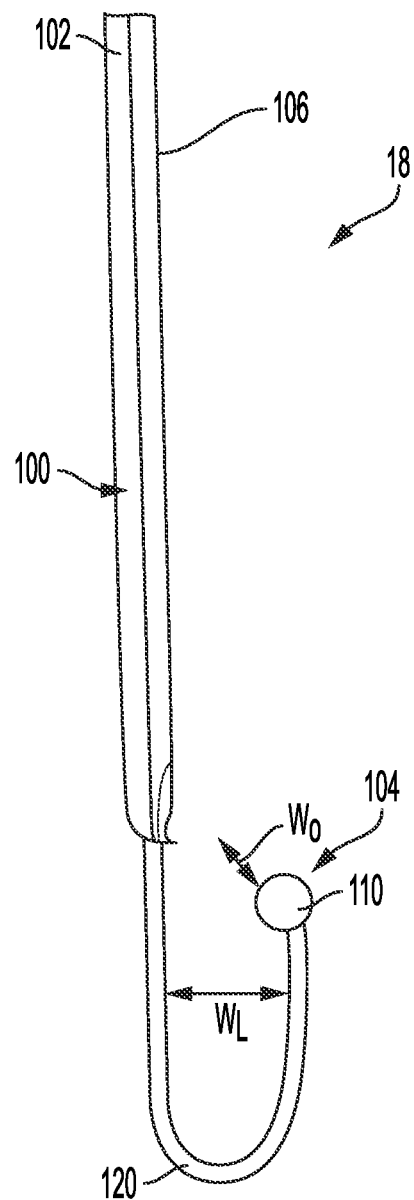
FIG. 2 illustrates a proximal end of a grasper protruding from a scope according to some examples of the present disclosure.

As shown in FIG. 2, the present invention 18 can comprise a grasper 100 with a distal end 102 and a proximal end 104 of a body 106. As shown, the grasper 100 is a passive device, "enveloping" an end of stent 16 via deft control of the spatial orientation of the grasper 100. There are no jaws, or other types of actuated elements that can damage the extraction process.

FIG. 2 illustrates a proximal end of a passive stent removal device configured to engage a stent for removal from a body, wherein the proximal end is a passive engagement end free of independently moving components like jaws or other conventional actuatable elements. The proximal end is configured to capture at least a portion of the stent via manipulation of the distal end of the grasper instrument through one or more actions selected from the group consisting of a pushing action, a pulling action, a twisting action, and a combination thereof and remove the stent from the body.

As shown, the proximal end of the grasper instrument can comprise a first proximal end portion that shares a common central axis with, and extends in the same direction as, the body portion, a second proximal end portion with a capture unit 110, the second proximal end portion extending in at least an approximately opposite direction from the first proximal end portion, and a u-shaped proximal end portion 120 connecting the first proximal end portion to the second proximal end portion.

The passive engagement end free of independently moving components has a loop width WL defined as the distance between the first proximal end portion and the second proximal end portion, and a capture opening width Wo defined as the smallest distance between the capture unit 110 and the first proximal end portion.

In an exemplary embodiment, the grasper 100 comprises diamond shaped medical stainless-steel wire, for example, 300 series stainless steel wire. 300 series stainless steel is also sometimes referred to as 18-8 grades. All 300 grades are austenitic. Austenitic grades will not gain strength after heat treatment. They gain their tensile and yield strength by cold working or drawing. 302, 304, and 316 stainless steel wire can be used since high strength and corrosion resistance is required. For added corrosion resistance 316 may be selected. It is lesser in strength than 302 but it offers improved corrosion characteristics due to the added Molybdenum.

The 304V alloy is electric-arc melted to refine the purity and homogeneity of the metal. This process yields a more uniform chemistry with minimal voids and contaminants. The ease of joining with solder or welding, combined with excellent strength makes it desirable.

The wire can be stainless steel, nitinol, PTFE coated & Parylene coated wire, with diameters ranging from 0.003"-0.145", of variables lengths and cross-sectional forms.

A ball 110 is located at the proximal end 104. The ball 110 can be formed from the wire of the grasper itself (wherein a TIG welder applies heat to the end of the wire, and the ball 110 formed from the melt), or can be a distinct element that is integrated at the end of the wire. In an exemplary form, the ball 110 is formed using a TIG welder soldering an end of the wire for less than a second. Additionally, using bending force, the end 104 can be bent to form a loop 120. The configuration of the loop/ball present the loop width WL, preferably from 0.1-0.2 inches, and the capture opening width Wo, preferably from 0.062-0.072 inches.

The body 106 can run a variety of lengths, but in exemplary embodiments, is 59 cm useful for short ureteroscopes and short, flexible and rigid cystoscopes, and 109 cm for long rigid and flexible ureteroscopes.

Figure 3:
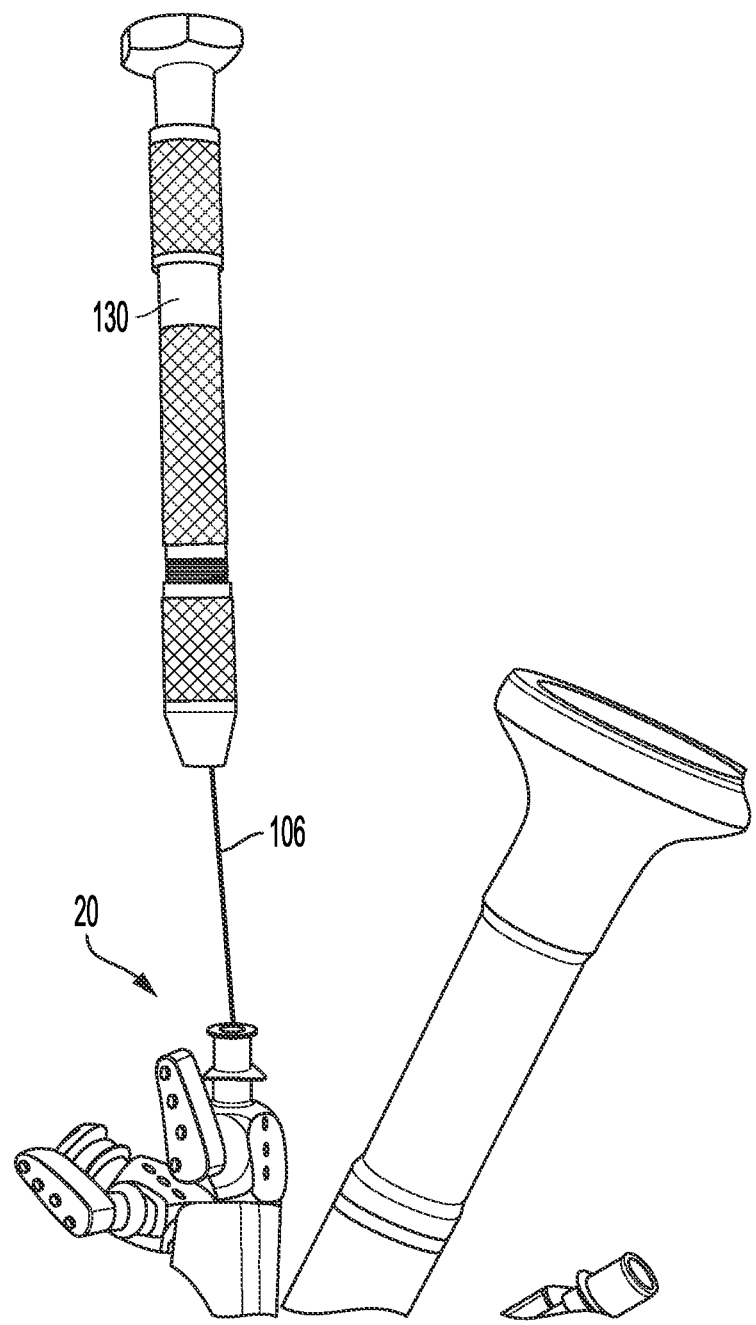
FIG. 3 illustrates a distal end of a grasper protruding from a scope and having a pin vise handle attached thereto according to some examples of the present disclosure.
Figure 7:
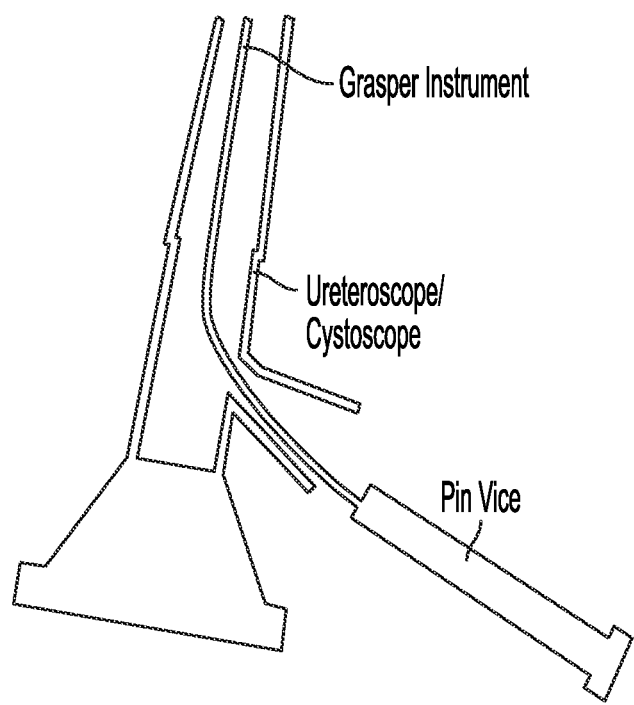
FIG. 7 illustrates that after backloading, a pin vice is attached to the loaded grasper instrument according to some examples of the present disclosure.
Figure 8:
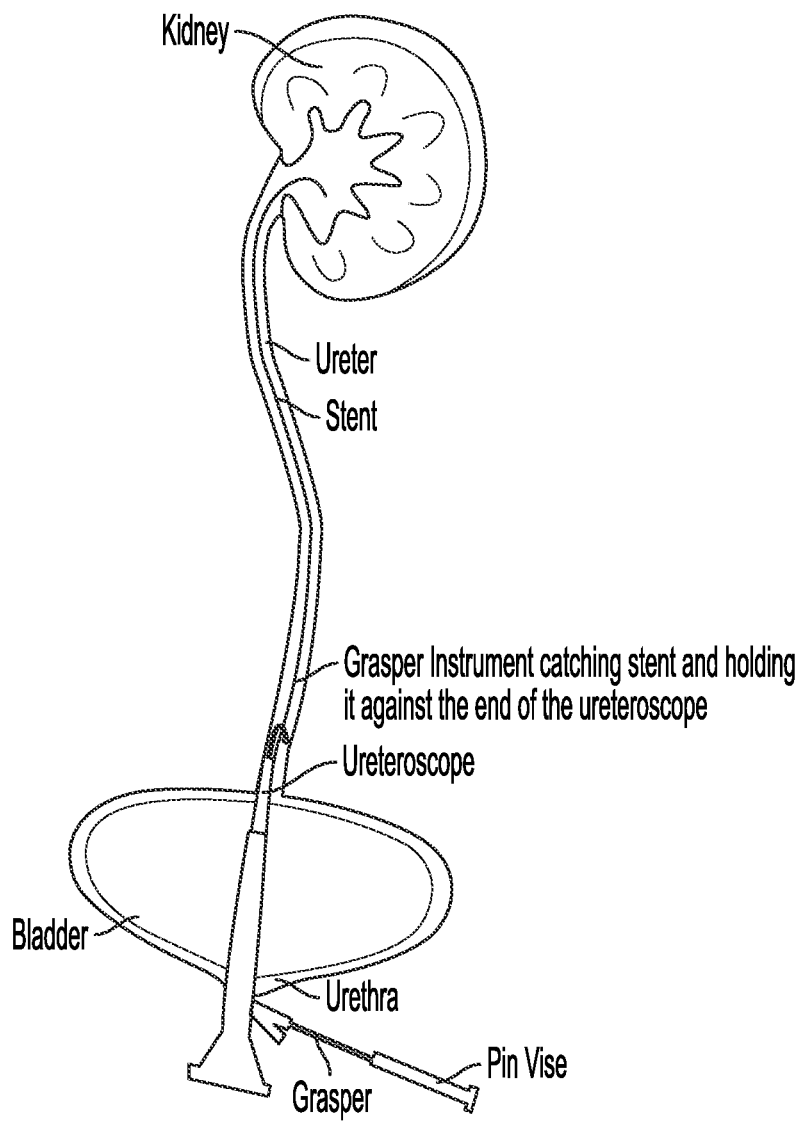
FIG. 8 illustrates an exemplary extraction of a stent with the present invention according to some examples of the present disclosure.

As shown in FIGS. 3 and 6-7, the grasper 100 can be back loaded though a ureteroscope/cystoscope 20, and a pin vise 130 then placed on the distal end 102 to control the orientation of the proximal end 104.

Other devices 130 can be used, including any tool holding device that allows small tools to be held in place with positive acting jaws with interchangeability depending on the effective diameters of the tool itself. Pin vises are available a few varieties, with tapered collets, insulated handles, double ends, and reduced lengths. to allow for a more rapid opening and closing of the chuck.

Figure 4:
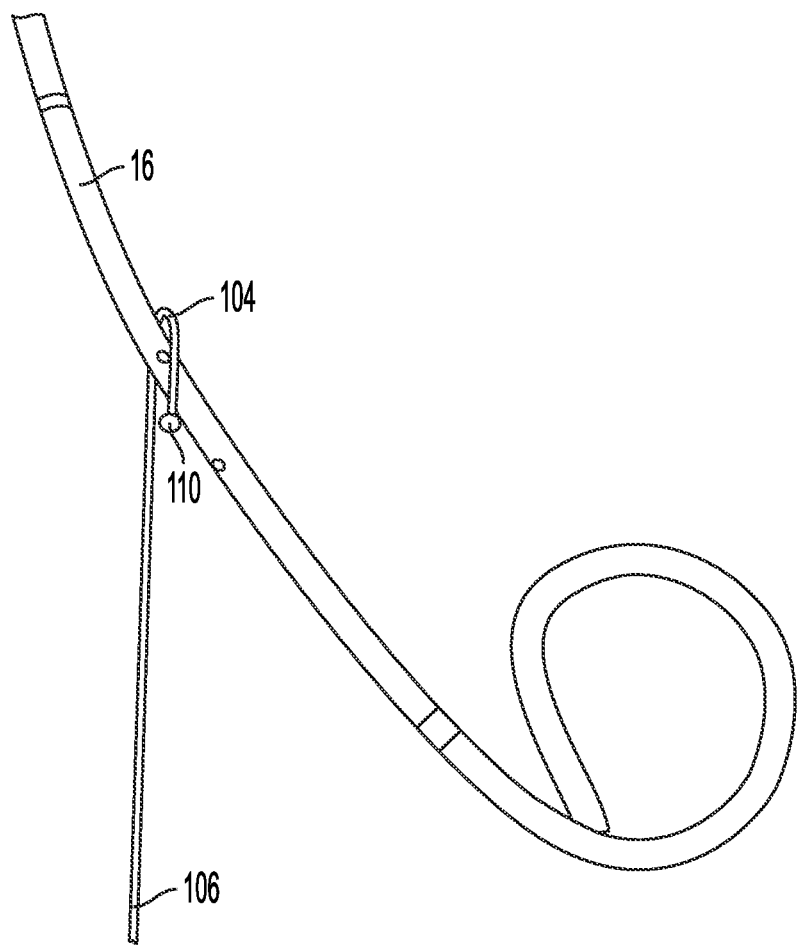
FIG. 4 illustrates a proximal end of a grasper with a stent captured by same according to some examples of the present disclosure.

As shown in FIGS. 4 and 6, the grasper 100 first captures a portion of a stent 16 in the loop portion, and then "pulls" the stent 16 snug against the end of the scope using the pin vise 130 to hold it in place.

The scope and grasper and stent are then removed together from the urinary system.

Those of skill in the art appreciate that sometimes a stent is in the ureter as opposed to the bladder. When this happens, conventional instruments are not very good because they are the grasper type and not strong enough to hold onto the stent to remove it. This disadvantage is overcome with the present invention, as the grasper 100 is strong enough to hold nearly any form or location of stent against the end of the ureteroscope and remove it. This ability is a big advantage of grasper 100 over conventional systems.

The stent 16 can be formed from one or more materials. The stent can be manufactured from one or more biocompatible plastics or polymers. For example, the stent can be formed from ethylene vinyl acetate (EVA), polytetrafluoroethylene (PTFE), silicone polyurethane, polyamide, polyurethane plastics, polyethylene plastics, and other thermoplastics and block copolymers thereof.

In other embodiments, the stent can be made from a metallic material such as stainless steel. In other embodiments, the stent can be manufactured from a superelastic or shape memory material. For example, a nickel-titanium alloy (e.g., nitinol) is a suitable superelastic or shape memory alloy for manufacturing the stent therefrom. In another embodiment, at least one portion of the stent can be coated.

Figure 5:
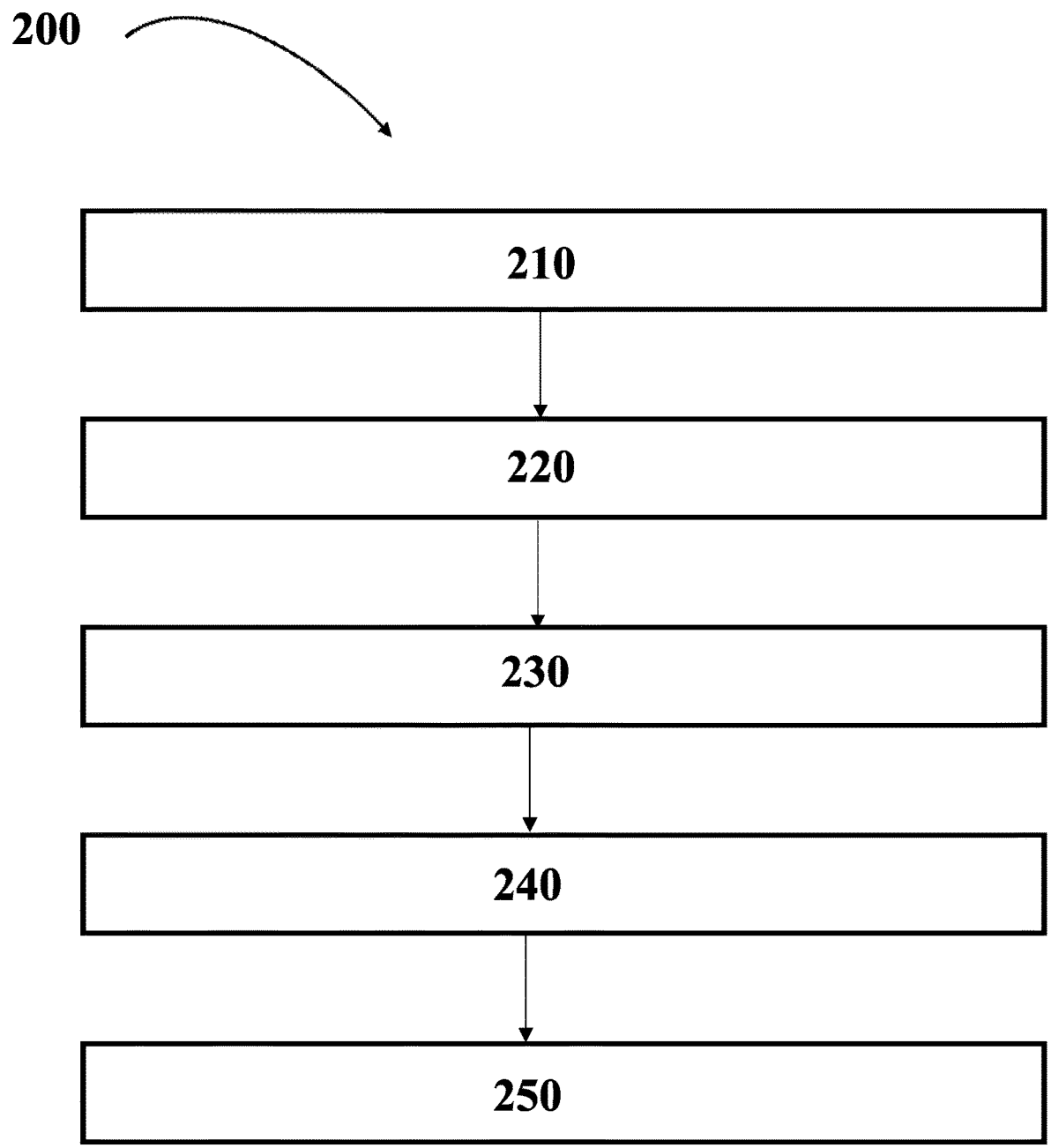
FIG. 5 is a flow diagram of an exemplary method of retraction according to some examples of the present disclosure.

As shown in FIG. 5, a method of grasping comprises an insertion step 210, backing loading a grasping device though a ureteroscope/cystoscope, a control step 220, including for example placing a pin vise about the distal end of grasping device to control the orientation of the proximal end of same, an initial capturing step 230, where a portion of the stent is caught in the loop portion of the grasping device, a subsequent securing step 240, where the grasping device is pulled in order to capture the stent snuggly against the end of the scope, and finally a retraction step 250, where the grasping device and stent are removed together from the urinary system.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. A passive stent removal device comprising:
a grasper instrument configured for back loading through an ureteroscope, the grasper instrument having a body portion between a proximal end extending beyond an insertion end of the ureteroscope to engage a ureteral stent for removal from a ureter and a distal end sized to pass through the ureteroscope and extend from a control end of the ureteroscope;
wherein the proximal end is a passive engagement end free of independently moving components to:
non-destructively capture at least a portion of the ureteral stent located in the ureter via manipulation of the distal end of the grasper instrument extending from the control end of the ureteroscope through one or more actions selected from the group consisting of a pushing action, a pulling action, a twisting action, and a combination thereof; and remove the ureteral stent from the ureter by securing the captured portion of the ureteral stent between the proximal end of the grasper instrument and an outer surface of the insertion end of the ureteroscope;

wherein the body portion extending from the distal end of the grasper instrument embodies dimensions so as to accommodate a working channel size of the ureteroscope;

wherein the proximal end is manipulatable within the ureter, the proximal end consisting of a single component comprising:

stainless steel wire;

a first proximal end portion sized to pass through the insertion end of the ureteroscope, the first proximal end portion sharing a common central axis with, and extending in the same direction as, the body portion;

a second proximal end portion with a sphere, which second proximal end remains outside of the insertion end of the ureteroscope during insertion of the passive stent removal device to engage and remove the ureteral stent from the ureter, the second proximal end portion extending in at least an approximately opposite direction from, and at a loop width distance apart from, the first proximal end portion, a capture opening width being defined as the smallest distance between the sphere of the second proximal end portion and the outer surface of the insertion end of the ureteroscope; and a u-shaped proximal end portion connecting the first proximal end portion to the second proximal end portion;

wherein the loop width is between 0.1-0.2 inches; and wherein the capture opening width is between 0.062-0.072 inches.

2. The passive stent removal device of claim 1, the passive engagement end free of independently moving components is free of actuated elements capable of movement independent from the manipulation of the distal end of the grasper instrument.

3. A method of removal of an indwelling stent from a ureter using the device of claim 1 comprising:

back loading the grasper instrument through the insertion end of the ureteroscope so the distal end of the grasper instrument extends from the control end of the ureteroscope;

inserting the proximal end of the grasper instrument into the ureter leading to an indwelling ureteral stent, wherein the second proximal end portion with the sphere remains outside of the insertion end of the ureteroscope during the inserting;

upon visual inspection, non-destructively capturing a portion of the ureteral stent in the ureter via manipulation of the distal end such that the captured portion of the ureteral stent fits through the capture opening width and into a loop portion of the grasper instrument defined by the first proximal end portion, the second proximal end portion, and the u-shaped proximal end portion; and removing the captured ureteral stent from the ureter via a pulling action at the distal end.

4. A passive stent removal system comprising:

a ureteroscope having a working channel, an insertion end, and a control end, the ureteroscope equipped with a light and camera, allowing visual inspection of a ureter; and a grasper instrument having a passive grasper end configured to be located within the ureter via insertion of the insertion end of the ureteroscope, and upon visual inspection, engage and remove a ureteral stent from the ureter, the passive grasper end comprising:

a ball end;

a first proximal end portion;

a second proximal end portion:

extending in an opposite direction from the first proximal end portion; and terminating at the ball end; and a loop proximal end portion connecting the first proximal end portion to the second proximal end portion;

wherein the ball end and the second proximal end portion are sized and designed to remain excluded from the working channel of the ureteroscope during insertion of the grasper instrument for use to remove the ureteral stent from the ureter;

wherein:

the grasper instrument further has a distal manipulation end extending from the control end of the ureteroscope when the grasper instrument is back loaded through the insertion end of the ureteroscope;

the grasper instrument further has and a body portion extending along a body axis, through the working channel, and extending a length between the passive grasper end and the distal manipulation end;

the first proximal end portion of the passive grasper end shares the body axis of the body portion and extends in the same direction as the body portion;

the passive grasper end is configured to non-destructively engage the ureteral stent for removal without independently actuatable elements to capture the ureteral stent; and the grasper instrument is of unitary construction such that through capture steps, manipulation of the distal manipulation end through orientations enables the passive grasper end to initially engage with at least a portion of the ureteral stent in the ureter, then capture at least a portion of the ureteral stent so it can be removed from the ureter, and then remove the captured ureteral stent.

5. The passive stent removal system of claim 4, wherein the second proximal end portion is separated by a loop width from the first proximal end portion;

wherein the loop width is smaller than an inner diameter of the ureter;

wherein a smallest distance between an outer surface of the ball end and the second proximal end portion is a capture opening width; and wherein the capture opening width is smaller than the loop width.

6. The passive stent removal system of claim 5, wherein the distal manipulation end is further operatively connected to a tool holding device through which an operator manipulates of the distal end of the grasper instrument through one or more actions selected from the group consisting of a pushing action, a pulling action, a twisting action, and a combination thereof.

7. A method of grasping comprising:

back loading a distal manipulation end of a grasping device though a ureteroscope from an insertion end of the ureteroscope, through a working channel of the ureteroscope, and out from a control end of the ureteroscope, wherein the back loading ceases when a portion of a proximal end of the grasping device is not insertable through the insertion end of the ureteroscope;

inserting the proximal end of the grasping device into a ureter via the ureteroscope while the portion of the proximal end of the grasping device not insertable through the insertion end of the ureteroscope remains outside of the ureteroscope; and upon visual inspection of an end portion of a ureteral stent located in the ureter and a location of the proximal end of the grasping device, capturing the end portion of the ureteral stent in the ureter via manipulation of the distal manipulation end such that a captured portion of the ureteral stent fits through a capture opening width and into a loop portion of the grasper instrument defined by a first proximal end portion, a second proximal end portion, and a u-shaped proximal end portion;

wherein:
the first proximal end portion is sized to pass through the insertion end of the ureteroscope;

the second proximal end portion has a sphere, the second proximal end portion remaining outside the ureteroscope during insertion, the second proximal end portion extending in at least an approximately opposite direction from, and at a loop width distance apart from, the first proximal end portion;

the capture opening width being defined as the smallest distance between the sphere of the second proximal end portion and an outer surface of the insertion end of the ureteroscope; and the u-shaped proximal end portion remaining outside the ureteroscope during insertion and connecting the first proximal end portion to the second proximal end portion.

8. The method of grasping of claim 7 further comprising: removing the ureteral stent from the ureter.

9. The method of grasping of claim 7, wherein the capturing is non-destructively capturing.

* * * * *